United States Patent [19]
Nakayasu et al.

[11] 4,299,978
[45] Nov. 10, 1981

[54] PROCESS FOR SEPARATING IMINODIACETIC ACID FROM AQUEOUS GLYCINE SOLUTION

[75] Inventors: Kazuo Nakayasu; Osamu Furuya; Yoshihiko Hosaki, all of Yokohama, Japan

[73] Assignee: Showa Denko Kabushiki Kaisha, Tokyo, Japan

[21] Appl. No.: 180,014

[22] Filed: Aug. 21, 1980

[51] Int. Cl.$^3$ ............................................. C07C 101/20
[52] U.S. Cl. ................................................. 562/554
[58] Field of Search ........................ 562/554, 575, 571

[56] References Cited

U.S. PATENT DOCUMENTS 3,813,434  5/1974  Marans ................................. 562/554
3,852,344 12/1974  Bragdon ............................... 562/554
3,875,221  4/1975  Mihara ................................. 562/554
3,947,496  5/1976  Thunberg .............................. 562/554

Primary Examiner—Natalie Trousof
Assistant Examiner—Michael Shippen
Attorney, Agent, or Firm—Armstrong, Nikaido, Marmelstein & Kubovcik

[57] ABSTRACT

A novel separation process of an iminodiacetic acid component from an aqueous glycine solution including the same is provided. In this process, sulfuric acid is added, in the presence of sodium salt, to the aqueous glycine solution in such an amount that the pH of the aqueous glycine solution becomes 1.5 or less, whereby the iminodiacetic acid is crystallized from the solution and, then, the crystallized iminodiacetic acid component is separated from the mother liquor. Thus, glycine can be efficiently recovered without causing undesirable accumulation of the iminodiacetic acid component in the mother liquor.

5 Claims, 1 Drawing Figure

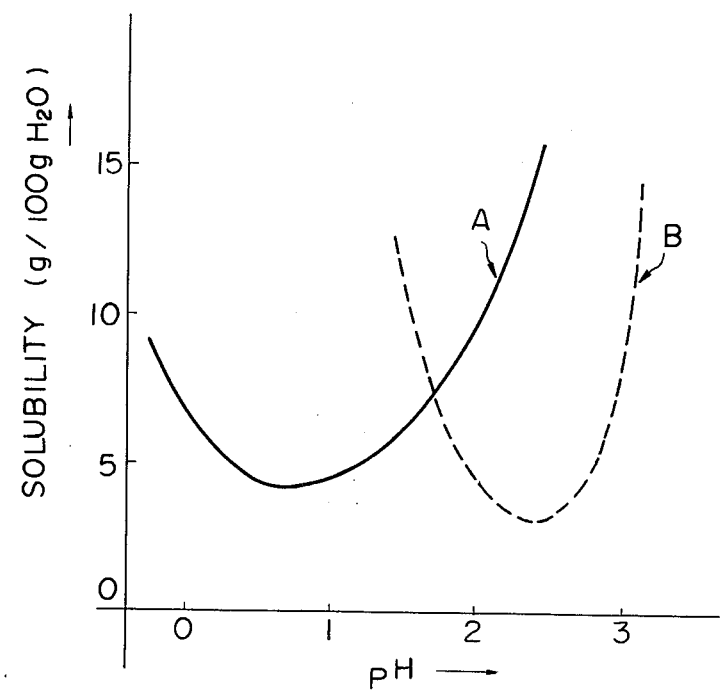

PROCESS FOR SEPARATING IMINODIACETIC ACID FROM AQUEOUS GLYCINE SOLUTION

The present invention relates to a process for separating an iminodiacetic acid component from an aqueous glycine solution including glycine or the salt thereof and iminodiacetic acid or the salt thereof. More specifically, it relates to a process for selectively crystallizing and separating the iminodiacetic acid component from the aqueous glycine solution by adding sulfuric acid, in the presence of a sodium salt, to the aqueous glycine solution in such an amount that the pH of the aqueous glycine solution becomes 1.5 or less.

The effective separation of iminodiacetic acid from an aqueous glycine solution including glycine or the salt thereof and iminodiacetic acid or the salt thereof is a very important technique in the commercial production of glycine. That is, glycine is conventionally produced as follows.

Glycinonitrile is hydrolyzed with an aqueous alkali metal hydroxide solution, whereby glycine in the form of the alkali metal salt is formed in the aqueous solution. Although only alkali metal hydroxide is specifically set forth herein for the sake of convenience, the term "alkali metal hydroxide" as used herein is intended to include the alkaline earth metal hydroxide, such as calcium hydroxide and magnesium hydroxide, together with the alkali metal hydroxide, such as sodium hydroxide, potassium hydroxide and the like. The resultant aqueous solution is then neutralized to the isoelectric point with an inorganic acid such as sulfuric acid or hydrochloric acid. Thus, an aqueous solution containing glycine and the neutral salt of the inorganic acid with the alkali metal hydroxide is formed. Glycine can be produced by the fractional crystallization of the glycine from the aqueous solution.

However, a small amount of iminodiacetic acid is produced as a by-product during the hydrolysis of the glycinonitrile and is present, together with the inorganic salt, in the aqueous glycine solution at the pH of the isoelectric point of glycine (i.e. approximately 6) as the mono alkali metal salt thereof. Since the amount of the by-product (i.e. iminodiacetic acid) is relatively small and, also, since the solubility of the alkali metal salt thereof in water is much higher than that of the glycine and the inorganic salt, the alkali metal salt of the iminodiacetic acid remains in the mother liquor without causing the crystallization of the iminodiacetic acid when the glycine and the inorganic salt are fractionally crystallized. According to a typical example of the conventional glycine separation and recovery methods, as set forth in, for example, British Pat. No. 1,472,840, an aqueous glycine-containing solution, which is previously neutralized with an inorganic acid, is first heated and concentrated, whereby the neutral salt of the inorganic acid is crystallized. The heating temperature is generally within the range of 105° to 116° C. The crystallized neutral salt of the inorganic acid is filtered out of the solution under a heated condition. The filtrate is then cooled to a temperature of 33° to 40° C. to crystallize the glycine. The crystallized glycine is thus fractionally recovered. Since the mother liquor still contains a large amount of glycine, together with the above-mentioned alkali metal salt of iminodiacetic acid, the mother liquor is recirculated to the above-mentioned glycine crystallization step, wherein the mother liquor is combined with a fresh aqueous glycine solution and is again subjected to the above-mentioned fractional crystallization operation.

However, in the case where the mother liquor is directly circulated to the glycine separation step, the alkali metal salt of the iminodiacetic acid having a high solubility in water is gradually accumulated in the circulated mother liquor. This accumulation of the alkali metal salt of the iminodiacetic acid in the mother liquor results in the following problems.

(1) The yield of the glycine obtained in one fractional crystallization operation is decreased.

(2) The glycine product is contaminated with the alkali metal salt of iminodiacetic acid. (Since glycine is mainly used for animal feed and food additives, the contamination with such impurity should be avoided.)

(3) The crystal size of the produced glycine becomes very fine and, as a result, the filtering operation thereof becomes difficult.

Furthermore, since the iminodiacetic acid is useful as a chelate compound, the separation and the recovery of the iminodiacetic acid from the above-mentioned aqueous glycine solution is also desired.

In order to prevent the excessive accumulation of the alkali metal salt of the iminodiacetic acid in the circulating mother liquor, a portion, or all, of the mother liquor may be continuously or intermittently withdrawn out of the circulating system (i.e. the renewal of the mother liquor). However, this results in unpreferable loss of the residual glycine in the mother liquor. In order to solve this problem, it has been proposed in British Pat. No. 1,472,840 and Japanese Patent Laid-Open Application No. 118421/77 that the iminodiacetic acid be selectively isolated from the mother liquor by adding an inorganic acid to at least a portion of the circulating mother liquor to adjust the pH of the mother liquor within the range of 2.4±0.5. This proposal is derived from the above-mentioned separation method of glycine, in which the alkali metal salt of glycine is neutralized to the vicinity of the isoelectric point thereof to crystallize glycine. That is, the above-mentioned proposal is based on the fact that the solubility of iminodiacetic acid in water is minimized in the vicinity of the isoelectric point thereof (i.e. pH=2.4±0.5). Nevertheless, this method involves a problem that one-pass recovery efficiency of the iminodiacetic acid is not satisfactory when the iminodiacetic acid is recovered from an aqueous solution containing, for example, glycine, sodium sulfate and mono sodium salt of iminodiacetic acid.

Accordingly, an object of the present invention is to obviate the above-mentioned problems of the prior art and to provide a process for selectively and efficiently separating an iminodiacetic acid component from an aqueous solution including glycine (or the salt thereof) and iminodiacetic acid (or the salt thereof).

Another object of the present invention is to prevent the accumulation of the iminodiacetic acid component in the circulating mother liquor without the renewal of the mother liquor in the above-mentioned recovery process of the glycine from an aqueous solution including glycine (or the salt thereof) and iminodiacetic acid (or the salt thereof).

Other objects and advantages of the present invention will be apparent from the description set forth hereinbelow.

In accordance with the present invention, there is provided a process for separating an iminodiacetic acid component from an aqueous glycine solution including the same comprising the steps of:

(a) adding sulfuric acid, in the presence of a sodium salt, to said aqueous glycine solution in such an amount that the pH of the aqueous glycine solution becomes 1.5 or less, preferably 0.4 through 1.2, whereby the iminodiacetic acid is crystallized from the solution, and;

(b) separating the crystallized iminodiacetic acid component from the mother liquor.

The present invention will be better understood from the description set forth below with reference to the accompanying graphical drawing illustrating the correlation between the solubility of iminodiacetic acid in water (g/100 gH$_2$O) and the pH of the solution in an aqueous solution including iminodiacetic acid.

In the drawing, curve A represents the correlation in the case of three components, that is, iminodiacetic acid-sodium sulfate-glycine and curve B represents the correlation in the case of a single component, that is, iminodiacetic acid.

For brevity's sake, in the description set forth below, the alkali metal (or alkaline earth metal) salt is exemplified by sodium salt. However, it should be noted that the sodium salt can be replaced by the other alkali metal salts and alkaline earth metal salts.

As mentioned hereinabove, an aqueous solution containing sodium salt of glycine and, as a by-product, a small amount of disodium salt of iminodiacetic acid can be obtained from the alkaline hydrolysis of glycinonitride in an aqueous solution by the addition of a stoichiometric amount of, or a slightly excessive amount of, sodium hydroxide. The starting glycinonitrile can be prepared, for example, by reacting formaldehyde and hydrocyanic acid, followed by the amination of the resultant glycolonitrile with ammonia.

The aqueous glycine solution prepared as mentioned above is then neutralized to a pH of approximately 6 through 7 by the addition of sulfuric acid, whereby an aqueous solution containing free glycine, sodium sulfate and mono sodium salt of iminodiacetic acid is obtained. As mentioned hereinabove, in order to recover glycine from this aqueous solution, it has been conventionally carried out that the aqueous glycine solution is first heated and concentrated to crystallize sodium sulfate in the solution and the crystallized sodium sulfate is filtered out of the solution under a heated condition. The glycine is fractionally crystallized from the resultant filtrate by cooling. Alternatively, glycine is first crystallized and separated from the aqueous glycine solution by cooling and, then, the sodium sulfate is crystallized by heating and filtered out of the solution under a heated condition. In both cases, the residual mother liquor still containing a large amount of glycine, together with mono sodium salt of iminodiacetic acid and sodium sulfate, is again returned to a fresh aqueous glycine solution for recovering the residual glycine, preferably after the removal of the iminodiacetic acid component.

As mentioned hereinabove, since the direct circulation of the mother liquor is not preferable due to the gradual accumulation of the iminodiacetic acid component in the circulating mother liquor, it has been proposed in British Pat. No. 1,472,840 that iminodiacetic acid be crystallized and separated from the mother liquor containing the same by adjusting the pH of the mother liquor within the range of 2.4±0.5. This method is based on the finding that, when an aqueous solution of monosodium salt of iminodiacetic salt is acidified by the addition of an inorganic acid such as sulfuric acid, the monosodium salt of iminodiacetic acid is converted to free iminodiacetic acid and the solubility of the iminodiacetic acid in water is lower than that of the monosodium salt and is minimized in the vicinity of a pH of 2.4.

It is true that the solubility of iminodiacetic acid in an aqueous solution containing only iminodiacetic acid is minimized at the isoelectric point thereof, that is, in the vicinity of a pH of 2.4 and the solubility thereof is incleased in the case where the aqueous solution is made acidic or basic from the isoelectric point by the addition of, for example, sulfuric acid or sodium hydroxide. However, the present inventors have surprisingly found that, in the case of the three component system of iminodiacetic acid-sodium sulfate-glycine, the solubility of iminodiacetic acid in an aqueous solution is not minimized in the vicinity of the pH of 2.4 of the isoelectric point, but minimized at a pH of 1.5 or less, especially within the range of 0.4 to 1.2.

The solubility of iminodiacetic acid (which is sometimes referred to as "IDA" hereinbelow) in an aqueous solution containing three components, that is, IDA, sodium sulfate (1 mol per 1 mol of IDA) and glycine (1 mol per 1 mol of IDA) at a room temperature obtained from the experimental data is illustrated as curve A in the accompanying graphical drawing. Curve B in the graphical drawing illustrates the solubility of IDA in an aqueous solution containing only IDA.

As is clear from the curves A and B in the accompanying drawing, the solubility of iminodiacetic acid in an aqueous solution containing the above-mentioned three components is remarkably small at a pH of 1.5 or less, preferably within the range of 0.4 to 1.2 and, therefore, the iminodiacetic acid can be selectively and efficiently separated from the above-mentioned mother liquor in the production of glycine.

The mechanism of the above-mentioned behavior of the iminodiacetic acid in the three component system at a pH of 1.5 or less is not clearly understood, but it would seem that, without prejudice to the present invention, the eutectic crystal of the sulfuric acid salt of iminodiacetic acid and sodium sulfate or the double salt of iminodiacetic acid and sodium bisulfate is crystallized, from the analytical data of the crystallized substance. Furthermore, in order to cause the above-mentioned behavior of iminodiacetic acid at a pH of 1.5 or less, the presence of a sodium salt in the aqueous solution is essential. For instance, in a case where a potassium salt, an ammonium salt, a calcium salt, a magnesium salt or the like is present in lieu of the sodium salt, the crystallization of iminodiacetic acid cannot be effected. Accordingly, in the case where alkaline compounds other than sodium compounds are employed in the alkaline hydrolysis step of glycinonitrile, sodium salts such as sodium sulfate, sodium chloride, sodium carbonate sodium bicarbonate, sodium formate and the like, preferably sodium sulfate, should be added to the mother liquor of the glycine separation step, prior to the crystallizing separation of the iminodiacetic acid from the mother liquor. The sodium salt is preferably present in an amount of at least 0.5 mol, based on 1 mol of the iminodiacetic acid and, more preferably, from 1 mol up to the saturated concentration.

For instance, an aqueous iminodiacetic acid solution containing (i) 13.3 g (0.1 mol) of iminodiacetic acid, (ii) 14.2 g (0.1 mol) of sodium sulfate, 17.4 g (0.1 mol) of potassium sulfate, a mixture of 7.1 g (0.05 mol) of sodium sulfate and 8.7 g (0.05 mol) of potassium sulfate or a mixture of 14.2 g (0.1 mol) sodium sulfate and 17.4 g (0.1 mol) of potassium sulfate and (iii) 50 ml of water is prepared. The pH of each solution is adjusted to 0.5 by the addition of 8.0 g of sulfuric acid. The resultant solution is cooled to a room temperature to crystallize the iminodiacetic acid. The crystallized iminodiacetic acid is recovered and weighed. The recovery efficiency of the iminodiacetic acid is shown in the following Table.

| Salt | Recovery Efficiency (%) |
|---|---|
| Na$_2$SO$_4$ (0.1 mol) | 80 |
| K$_2$SO$_4$ (0.1 mol) | 1 |
| Na$_2$SO$_4$ (0.05 mol) + K$_2$SO$_4$ (0.05 mol) | 56 |
| Na$_2$SO$_4$ (0.1 mol) + K$_2$SO$_4$ (0.1 mol) | more than 80 |

As mentioned above, according to the present invention, since the iminodiacetic acid present in the mother liquor is crystallized and separated, for example, by filtration, from the mother liquor by acidifying a portion of, or all of the circulating mother liquor to a pH of 1.5 or less, the mother liquor can be advantageously combined with a fresh aqueous glycine solution, optionally after the mother liquor is decolored with activated carbon. Thus, the neutralization step and the fractional crystallization step of the glycine can be repeatedly and smoothly carried out without causing the unpreferable accumulation of iminodiacetic acid in the mother liquor. It should be noted that all of the circulating mother liquor is not subjected to the acidifying treatment, but a portion thereof can be subjected to the acidifying treatment in such a manner that the concentration of the iminodiacetic component does not become excessive (that is, the concentration is preferably kept below about 6% by weight).

The foregoing specific embodiments have been disclosed only for the continuous operation in which the mother liquor is combined with a fresh aqueous glycine solution. However, it should be noted that the mother liquor is repeatedly used for selectively recovering glycine from the mother liquor in a manner as mentioned hereinabove. The iminodiacetic acid component (i.e. the above-mentioned eutectic crystal or double salt), which is separated from the aqueous glycine solution by the acidification of the solution to a pH of 1.5 or less, is again dissolved in water and the iminodiacetic acid can be recovered from this aqueous solution by adjusting a pH of the solution within the range of 1.9 to 2.9.

As mentioned hereinabove, according to the present invention, an iminodiacetic acid component can be selectively and effectively recovered from an aqueous solution containing glycine and iminodiacetic acid in the form of a free acid and/or the salt thereof and glycine can be efficiently obtained from the aqueous glycine solution without the renewal of the mother liquor.

The present invention is now illustrated by, but is by no means limited to, the following examples.

EXAMPLES 1 TO 8

An aqueous glycinonitrile solution was prepared from an aqueous glycolonitrile solution containing 48.9% by weight of glycolonitrile and 0.2% by weight of hydrocyanic acid and ammonia in a conventional manner as described in J. Am. Chem. Soc., 56, 2197 (1934). From the resultant slightly brown aqueous solution, the unreacted ammonia was removed at atmospheric pressure and, then, a 48% by weight aqueous sodium hydroxide solution was added to the aqueous glycinonitrile solution in an amount of 1.05 mol of sodium hydroxide per 1 mol of glycinonitrile and was allowed to react with the glycinonitrile at a temperature of 100° C. for 1 hour.

An aqueous solution of the sodium salt of glycine having the following composition was obtained.

| Composition | % by weight |
|---|---|
| Sodium Salt of Glycine | 34.4 |
| Sodium Salt of Iminodiacetic Acid | 1.1 |
| Sodium Hydroxide | 1.3 |
| Water | 63.2 |

This aqueous solution was subjected to the following fractional crystallization operation.

A. First Step (Neutralization)

The aqueous solution obtained above was neutralized to a pH of 6 through 7 with 98% by weight sulfuric acid.

B. Second Step (Fractional Crystallization)

The aqueous solution neutralized in the first step was heated to the boiling point and concentrated, whereby sodium sulfate was crystallized in the solution. The concentration of the aqueous solution was stopped just before the glycine in the aqueous solution began to crystallize. The crystallized sodium sulfate was separated from the aqueous solution under the heated state by means of a centrifugal separator. The filtrate was cooled to a temperature of approximately 34° C. to crystallize the glycine. The crystallized glycine was separated from the aqueous solution by means of a centrifugal separator. The filtrate was recovered as a mother liquor. The by-produced iminodiacetic acid remained in this filtrate in the form of the mono sodium salt thereof.

C. Third Step (Fractional Crystallization)

The mother liquor obtained in the second step was again heated to the boiling point and concentrated, whereby sodium sulfate was again crystallized. The heating was stopped just before the glycine in the solution began to crystallize. The crystallized sodium sulfate was separated from the aqueous solution under a heated state by means of a centrifugal separator. The filtrate was cooled to a temperature of approximately 34° C., whereby the glycine in the aqueous solution was crystallized. The crystallized glycine was recovered by means of a centrifugal separator. The filtrate was also recovered as a mother liquor.

The above-mentioned operation was further repeated twice.

D. Fourth Step (Recovery of Iminodiacetic Acid)

The mother liquor in which the content of the mono sodium salt of iminodiacetic acid was moderately concentrated was obtained after the fractional crystallization operation of sodium sulfate and glycine was repeated three times in the third step. The composition of the resultant mother liquor was as follows.

| Composition | % by weight |
|---|---|
| Glycine | 13.9 |
| Mono Sodium Salt of Iminodiacetic Acid | 18.2 |
| Sodium Sulfate | 14.4 |
| Water | 53.5 |

200 g each of the mother liquor was stirred at a room temperature (approximately 20° C.) for 3 hours under various pH conditions listed in Table I below. The resultant crystallized precipitate was filtered with suction. Thus, cake and filtrate were obtained. The results are shown in the following Table I.

TABLE I

| Example No. | Liquid pH at[1] Crystallization | Weight of[2] Cake (g) | Content of[3] in IDA Cake (wt %) | Recovery[4] Efficiency of IDA (%) |
|---|---|---|---|---|
| 1 | 0.0 | 79 | 34 | 86 |
| 2 | 0.45 | 74 | 38 | 90 |
| 3 | 0.8 | 80 | 36 | 92 |
| 4 | 1.2 | 83 | 34 | 90 |
| 5 | 1.5 | 74 | 36 | 85 |
| 6 | 1.8 | 61 | 36 | 70 |
| 7 | 2.3 | 47 | 36 | 54 |
| 8 | 2.7 | 29 | 38 | 35 |

[1] The pH was adjusted with about 80% Sulfuric Acid.
[2] The weight of the cake was weighed after 16 hours during at 105° C.
[3] The weight of the iminodiacetic acid (IDA) was converted to a free acid basis.
[4] $\dfrac{\text{Weight of IDA in cake}}{\text{Weight of IDA in 200 g of Mother Liquor (31.2 g)}} \times 100$ As is clear from the results shown in Table I, the recovery efficiency of the iminodiacetic acid was high within the range of a pH of 0.0 to 1.5. The recovery efficiency was decreased as the pH was increased. The purity of the recovered iminodiacetic acid was not affected by the pH condition. No substantial amount of glycine was crystallized together with the iminodiacetic acid and 90% or more of the glycine remained in the resultant mother liquor.

The cake obtained in Example 3 was dissolved in water and the aqueous solution was decolored with a small amount of activated carbon. After the filtration, an aqueous sodium hydroxide solution was added to the aqueous solution in an amount such that the pH of the aqueous solution became 2.4. The aqueous solution was then heated and concentrated just before the sodium sulfate contained in the solution began to crystallize. The concentrated solution was allowed to cool with stirring, whereby the iminodiacetic acid was gradually crystallized. The crystallized iminodiacetic acid was filtered at a temperature of the aqueous solution of 34° C. The filtered crystals were washed with water and then dried. Thus, 22.7 g of white crystals were obtained. The recovery efficiency of the iminodiacetic acid from the mother liquor was 73% and the recovery efficiency from the cake was 79%.

We claim:

1. A process for separating an iminodiacetic acid component from an aqueous glycine solution including the same comprising the steps of:
    (a) adding sulfuric acid, in the presence of a sodium salt, to said aqueous glycine solution in such an amount that the pH of the aqueous glycine solution becomes 1.5 or less, whereby the iminodiacetic acid is crystallized from the solution, and;
    (b) separating the crystallized iminodiacetic acid component from the mother liquor.

2. A process as claimed in claim 1, wherein said pH of the aqueous glycine solution is within the range of 0.4 to 1.2.

3. A process as claimed in claim 1, wherein the amount of the sodium salt present in the aqueous glycine solution is at least 0.5 mol, based on 1 mol of the iminodiacetic acid component present in the solution.

4. A process as claimed in claim 1, wherein said mother liquor is transferred to a glycine separation step after the mother liquor is decolored with activated carbon.

5. A process as claimed in claim 1, wherein the separated iminodiacetic acid is dissolved in water and, then the pH of the aqueous iminodiacetic acid is adjusted to a range of 1.9 to 2.9, whereby iminodiacetic acid is recovered.

* * * * *